(12) United States Patent
Haran

(10) Patent No.: US 7,321,425 B2
(45) Date of Patent: Jan. 22, 2008

(54) SENSOR AND METHODS FOR MEASURING SELECT COMPONENTS IN SHEETMAKING SYSTEMS

(75) Inventor: Frank M. Haran, North Vancouver (CA)

(73) Assignee: Honeywell International Inc., Morristown, NJ (US)

( * ) Notice: Subject to any disclaimer, the term of this patent is extended or adjusted under 35 U.S.C. 154(b) by 367 days.

(21) Appl. No.: 11/018,167

(22) Filed: Dec. 20, 2004

(65) Prior Publication Data

US 2006/0132796 A1 Jun. 22, 2006

(51) Int. Cl.
*G01J 3/28* (2006.01)
*G01J 3/06* (2006.01)
*G01J 5/02* (2006.01)

(52) U.S. Cl. .................. 356/326; 356/308; 250/339.01
(58) Field of Classification Search ...................... None
See application file for complete search history.

(56) References Cited

U.S. PATENT DOCUMENTS

| | | | |
|---|---|---|---|
| 4,311,658 A | 1/1982 | Nicoll | 264/175 |
| 4,490,845 A * | 12/1984 | Steinbruegge et al. | 356/300 |
| 4,505,550 A | 3/1985 | Steinbruegge | 350/372 |
| 4,797,246 A | 1/1989 | Reinke et al. | 264/504 |
| 4,879,471 A | 11/1989 | Dahlquist | 250/359.1 |
| 4,885,709 A | 12/1989 | Edgar et al. | |
| 5,013,403 A | 5/1991 | Chase | 162/49 |
| 5,039,855 A * | 8/1991 | Kemeny et al. | 250/339.07 |
| 5,094,535 A | 3/1992 | Dahlquist et al. | 356/346 |
| 5,166,748 A | 11/1992 | Dahlquist | 356/346 |
| 5,230,923 A | 7/1993 | Hirokawa et al. | 427/248.1 |
| 5,235,192 A * | 8/1993 | Chase et al. | 250/559.11 |
| 5,276,327 A | 1/1994 | Bossen et al. | 250/339 |
| 5,438,406 A | 8/1995 | Puschell | 356/307 |
| 5,444,528 A | 8/1995 | Puschell | 356/73 |
| 5,541,413 A | 7/1996 | Pearson et al. | 250/339.11 |
| 5,606,413 A * | 2/1997 | Bellus et al. | 356/326 |
| 5,795,394 A | 8/1998 | Belotserkovsky et al. | 118/665 |
| 5,821,536 A * | 10/1998 | Pettit | 250/339.1 |
| 5,891,306 A | 4/1999 | Chase et al. | 162/198 |
| 5,965,888 A * | 10/1999 | Engstrom et al. | 250/339.09 |

(Continued)

FOREIGN PATENT DOCUMENTS

DE 10031636 1/2002

(Continued)

*Primary Examiner*—Gregory J. Toatley, Jr.
*Assistant Examiner*—Jonathan Skovholt
(74) *Attorney, Agent, or Firm*—Munck Butrus Carter, PC (57) ABSTRACT

A sensor for measuring at least selected component in a composition can include: (a) a broadband light source, (b) an acousto-optic tunable filter (AOTF), (c) means for generating a beam of light from the light source and directing the beam of light at the AOTF wherein the AOTF is tuned to pass detection light having a desired wavelength range to detect the presence of the at least one component in the composition, (d) means for directing the detection light of known wavelength to the composition, (e) detection means for receiving light that emerges from the composition, and (f) a control signal generator configured to provide the AOTF with at least one desired wavelength range that is characteristic of the least one component in the composition. As an example, the sensor can be used to measure the thickness of optically transparent films.

35 Claims, 4 Drawing Sheets

U.S. PATENT DOCUMENTS

| | | | |
|---|---|---|---|
| 6,031,233 A * | 2/2000 | Levin et al. | 250/339.11 |
| 6,262,419 B1 * | 7/2001 | Huth-Fehre et al. | 250/341.8 |
| 6,565,343 B1 | 5/2003 | Krycki | 425/72.1 |
| 6,643,060 B2 | 11/2003 | Hashimoto et al. | 359/346 |
| 6,780,284 B2 | 8/2004 | Almi et al. | 162/198 |
| 6,793,854 B1 | 9/2004 | Kirjavainen | 264/45.9 |
| 6,816,636 B2 | 11/2004 | Cole et al. | 385/10 |
| 6,822,785 B1 | 11/2004 | Chu et al. | 359/308 |
| 2004/0124366 A1 * | 7/2004 | Zeng et al. | 250/458.1 |
| 2004/0246493 A1 * | 12/2004 | Kim et al. | 356/504 |
| 2005/0122529 A1 * | 6/2005 | Kim et al. | 356/503 |

FOREIGN PATENT DOCUMENTS

| | | |
|---|---|---|
| WO | WO 97/08537 | 3/1997 |
| WO | WO 9902941 | 1/1999 |
| WO | WO 0031521 | 6/2000 |

* cited by examiner

SENSOR AND METHODS FOR MEASURING SELECT COMPONENTS IN SHEETMAKING SYSTEMS

FIELD OF THE INVENTION

The present invention generally relates to systems for controlling continuous sheetmaking systems and, more specifically, to sensors and methods for measuring the concentration of specific components in paper, plastic, and the like. The technique employs a device that directs infrared radiation within a specific wavelength band onto the sheet of material and detects the radiation which emerges from the material.

BACKGROUND OF THE INVENTION

In the art of modern high-speed papermaking, it is well known to continuously measure certain properties of the paper material in order to monitor the quality of the finished product. These on-line measurements often include basis weight, moisture content, and sheet caliper, i.e., thickness. The measurements can be used for controlling process variables with the goal of maintaining output quality and minimizing the quantity of product that must be rejected due to disturbances in the manufacturing process.

Similarly, in the production of plastics it is known that specific polymers can be identified by their characteristic absorption peaks when exposed to radiation having certain wavelengths. Indeed, such on-line measurements can be employed to detect the presence and concentrations of specific polymers in the production, disposable, or recycling of plastic articles.

The on-line sheet property measurements are often accomplished by scanning sensors that periodically traverse the sheet material from edge to edge. For example, a high-speed scanning sensor may complete a scan in a period as short as twenty seconds, with measurements being read from the sensor at about 50 milliseconds intervals. A series of stationary sensors can also be used to make similar on-line measurements.

In the manufacture of paper on continuous papermaking machines, a web of paper is formed from an aqueous suspension of fibers (stock) on a traveling mesh papermaking fabric and water drains by gravity and suction through the fabric. The web is then transferred to the pressing section where more water is removed by pressure and vacuum. The web next enters the dryer section where steam heated dryers and hot air completes the drying process. The paper machine is, in essence, a water removal, system. A typical forming section of a papermaking machine includes an endless traveling papermaking fabric or wire, which travels over a series of water removal elements such as table rolls, foils, vacuum foils, and suction boxes. The stock is carried on the top surface of the papermaking fabric and is de-watered as the stock travels over the successive de-watering elements to form a sheet of paper. Finally, the wet sheet is transferred to the press section of the papermaking machine where enough water is removed to form a sheet of paper. Papermaking devices well known in the art are described for example in Handbook for Pulp & Paper Technologists 2nd ed., G. A. Smook, 1992, Angus Wilde Publications, Inc., and Pulp and Paper Manufacture Vol III (Papermaking and Paperboard Making), R. MacDonald, ed. 1970, McGraw Hill. Sheetmaking systems are further described, for example, in U.S. Pat. No. 5,539,634 to He, U.S. Pat. No. 5,022,966 to Hu, U.S. Pat. No. 4,982,334 to Balakrishnan, U.S. Pat. No. 4,786,817 to Boissevain et al., and U.S. Pat. No. 4,767,935 to Anderson et al. Many factors influence the rate at which water is removed which ultimately affects the quality of the paper produced. As is apparent, it would be advantageous to monitor the final paper product so as to, among other things, predict and control the dry stock weight of the paper that is produced.

It is conventional to measure the moisture content of sheet material upon its leaving the main dryer section or at the take up reel employing scanning sensors. Such measurement may be used to adjust the machine operation toward achieving desired parameters. One technique for measuring moisture content is to utilize the absorption spectrum of water in the infrared region. A monitoring or gauge apparatus for this purpose is commonly in use. Such apparatus conventionally use either a fixed gauge or a gauge mounted on a scanning head which is repetitively scanned transversely across the web at the exit from the dryer section and/or upon entry to the take up reel, as required by the individual machines. The gauges typically use a broad-band infrared source and one or more detectors with the wavelength of interest being selected by a narrow-band filter, for example, an interference type filter. The gauges used fall into two main types: the transmissive type in which the source and detector are on opposite sides of the web and, in a scanning gauge, are scanned in synchronism across it, and the scatter type (sometimes called "reflective" type) in which the source and detector are in a single head on one side of the web, the detector responding to the amount of source radiation scattered from the web.

Although it is most common to position IR moisture gauges in the more benign dry-end environment, similar gauges are also employed in the wet-end of the paper machine. The wet-end moisture gauges are typically located at the end of the press section or the beginning of the dryer section. Gauges in these locations are useful for diagnosis of press and forming sections of the paper machine, or for 'setting up' the web for entry into the dryer section.

Plastics films can be manufactured in a variety of ways. Typically, raw materials such as thermoplastics are fluxed into a rubber-like mass and then passed through a series of nips formed by a number of heated cooperating rolls to form a film, sheet or web of the specified thickness. In addition, different types of polymer films can be laminated together to form multilayer films. It is desired for process control to monitor the thickness of films produced.

Many of the current spectroscopic type sensors rely on non-versatile, non-generic techniques to detect various characteristics or constituents of paper and polymer products. These prior art techniques typically use passive bulk optic components such as beam splitters (either amplitude or dichoric) and individual fixed filters. As is apparent, one disadvantage is that these sensors cannot be readily reconfigured to detect different constituents. In addition, it is difficult to employ an optimum filter bandwidth or to move the filter's center wavelength to compensate for temperature induced wavelength shifts in a spectroscopic material feature. Prior art sensors also do not afford the versatility of permitting a switch from a first mode of operation in which the weights of various constituents are detected using spectroscopic techniques to a second mode of operation in which the coating thickness, for example, is measured using interferometric techniques. Specifically, with interferometric techniques, it is particularly useful to employ a wavelength diverse method that has the capacity of tuning over a certain wavelength range at a particular spectral resolution which will be dependent upon the optical thickness, which is a product of refractive index and physical thickness, for the particular coating of interest. Such versatility is not attainable with prior art sensors using fixed width and position filters. Finally, measuring numerous constituents in a flat sheet with prior art discrete filters entails a correspondingly large number of detectors and filters. Given that signals have to be split many times, signal strength will be adversely affected with a concomitant reduction in the signal-to-noise ratio.

Prior art gauges were generally hardware configured for a particular application. This entailed defining a number of channels, typically in the range from 2 to 12 or more wavelength channels each with a specific filter with its own specific center wavelength and spectral width. This process is labor intensive, costly and inefficient, and moreover, the gauges included many redundant components.

SUMMARY OF THE INVENTION

The present invention is based in part on the recognition that an efficient and versatile spectrometric sensor can be configured with an acousto-optic tunable filter. With this diverse spectral filter, the central wavelength and bandwidth of the filter can be quickly tuned to the desired wavelength.

In one embodiment, the invention is directed to a sensor, for measuring the basis weight of at least one selected component in a composition, that includes:
  (a) a broadband light source;
  (b) an acousto-optic tunable filter (AOTF);
  (c) means for generating a beam of light from the light source and directing the beam of light at the AOTF wherein the AOTF is tuned to pass detection light having a desired wavelength range to detect the presence of the at least one component in the composition;
  (d) means for directing the detection light of known wavelength to the composition;
  (e) detection means for receiving light that emerges from the composition; and
  (f) a program structure that is coupled to the AOTF, the program structure capable of providing the AOTF with at least one desired wavelength range that is characteristic of the least one component in the composition.

In another embodiment, the invention is directed to a sensor, for measuring the thickness of an optically transparent film, that includes:
  (a) a broadband light source;
  (b) an acousto-optic tunable filter (AOTF);
  (c) means for generating a beam of light from the light source and directing the beam of light at the AOTF wherein the AOTF is dynamically tuned over a range of wavelengths that can produce interference in the transparent film;
  (d) means for directing a collimated detection light of known wavelength to the film;
  (e) detection means for receiving light that emerges from the film; and
  (f) a program structure that is coupled to the AOTF, the program structure capable of providing the AOTF with at least one desired wavelength range that is capable of producing interference in the transparent film.

In another embodiment, the invention is directed to a sensor, for measuring the basis weight of at least one selected component in a composition, that includes:
  (a) a broadband light source that generates light that is directed to the composition;
  (b) an acousto-optic tunable filter (AOTF) positioned to receive light that emerges from the composition wherein the AOTF is tuned to pass detected light having a desired wavelength range to detect the presence of the at least one component in the composition;
  (c) detection means for receiving the detected light; and
  (d) a program structure that is coupled to the AOTF, the program structure capable of providing the AOTF with at least one desired wavelength range that is characteristic of the least one component in the composition.

In yet another embodiment, the invention is directed to a sensor, for measuring the thickness of an optically transparent film, that includes:
  (a) a broadband light source that generates light that is directed to the film;
  (b) an acousto-optic tunable filter (AOTF) positioned to receive light that emerges from the film wherein the AOTF is dynamically tuned over a range of wavelengths that can produce interference in the transparent film;
  (c) detection means for receiving a collimated detected light; and
  (d) a program structure that is coupled to the AOTF, the program structure capable of providing the AOTF with at least one desired wavelength range that is capable of producing interference in the transparent film.

In a further embodiment, the invention is directed to a method for measuring the amount of at least one select component of a composition that includes the steps of:
  (a) directing broadband light to an acousto-optic tunable filter (AOTF);
  (b) tuning the AOTF to pass a first detection light having a desired wavelength to detect the presence of the a first component in the composition;
  (c) directing the first detection light to the composition;
  (d) detecting the intensity of the first detection light that emerges from the composition;
  (e) tuning the AOTF to change the wavelength of the detection light to generate a second detection light to measure a second component in the composition;
  (f) directing the second detection light to the composition;
  (g) detecting the intensity of the second detection light that emerges from the composition;
  (h) optionally, repeating steps (f) and (g) but for different wavelengths in order to measure one or more components other than the first and second components; and
  (i) optionally, measuring the temperature of the composition and changing the wavelength of the first or second detection light to optimize sensitivity to the particular components that are of interest in detecting.

In a still another embodiment, the invention is directed to a method for measuring the thickness of an optically transparent film that includes the steps of:
  (a) directing broadband light to an acousto-optic tunable filter (AOTF);
  (b) dynamically tuning the AOTF to pass a first detection light having a desired swept wavelength band to produce interference in the optically transparent film;
  (c) directing the first detection light to the film;
  (d) detecting the intensity of the first detection light that emerges from the film;
  (e) detecting the change in intensity of the first detection light as the interference condition for the thickness of the optically transparent film is achieved; and
  (f) calculating the film thickness using the wavelength that produced the interference condition.

In a further embodiment, the invention is directed to a method for measuring basis weight of at least one select component of a composition that includes the steps of:

(a) directing broadband light to the composition;
(b) directing light that emerges from the composition into an acousto-optic tunable filter (AOTF);
(c) tuning the AOTF to pass a first detection light having a desired wavelength to detect the presence of the a first component in the composition;
(d) detecting the intensity of the first detection light that emerges from the composition;
(e) tuning the AOTF to change the wavelength of the detection light to generate a second detection light to measure a second component in the composition;
(f) detecting the intensity of the second detection light that emerges from the composition;
(g) optionally, repeating steps (e) and (f) but for different wavelengths in order to measure one or more components other than the first and second components; and
(h) optionally, measuring the temperature of the composition and changing the wavelength of the first or second detection light to optimize the intensity of the detection light that is measured.

Finally, in another embodiment, the invention is directed to a method for measuring the thickness of an optically transparent film that includes the steps of:
(c) directing broadband light to the film;
(d) directing light that emerges from the film into an acousto-optic tunable filter (AOTF);
(c) dynamically tuning the AOTF to pass a first detection light having a desired swept wavelength band to produce interference in the optically transparent film;
(d) detecting the intensity of the first detection light that emerges from the film;
(e) detecting the change in intensity of the first detection light as the interference condition for the thickness of the optically transparent film is achieved; and
(f) calculating the film thickness using the wavelength that produced the interference condition.

DETAILED DESCRIPTION OF PREFERRED EMBODIMENTS

The present invention relates to a sensor apparatus for detecting properties of a composition, especially material that is in the form of a film, web or sheet. While the sensor will be illustrated in measuring paper and plastic products, it is understood that the sensor can be employed to detect properties in other materials including, for example, coated materials and fabrics and the like. The sensor apparatus can also measure the thickness of optically transparent film and the like.

Figure 1A:
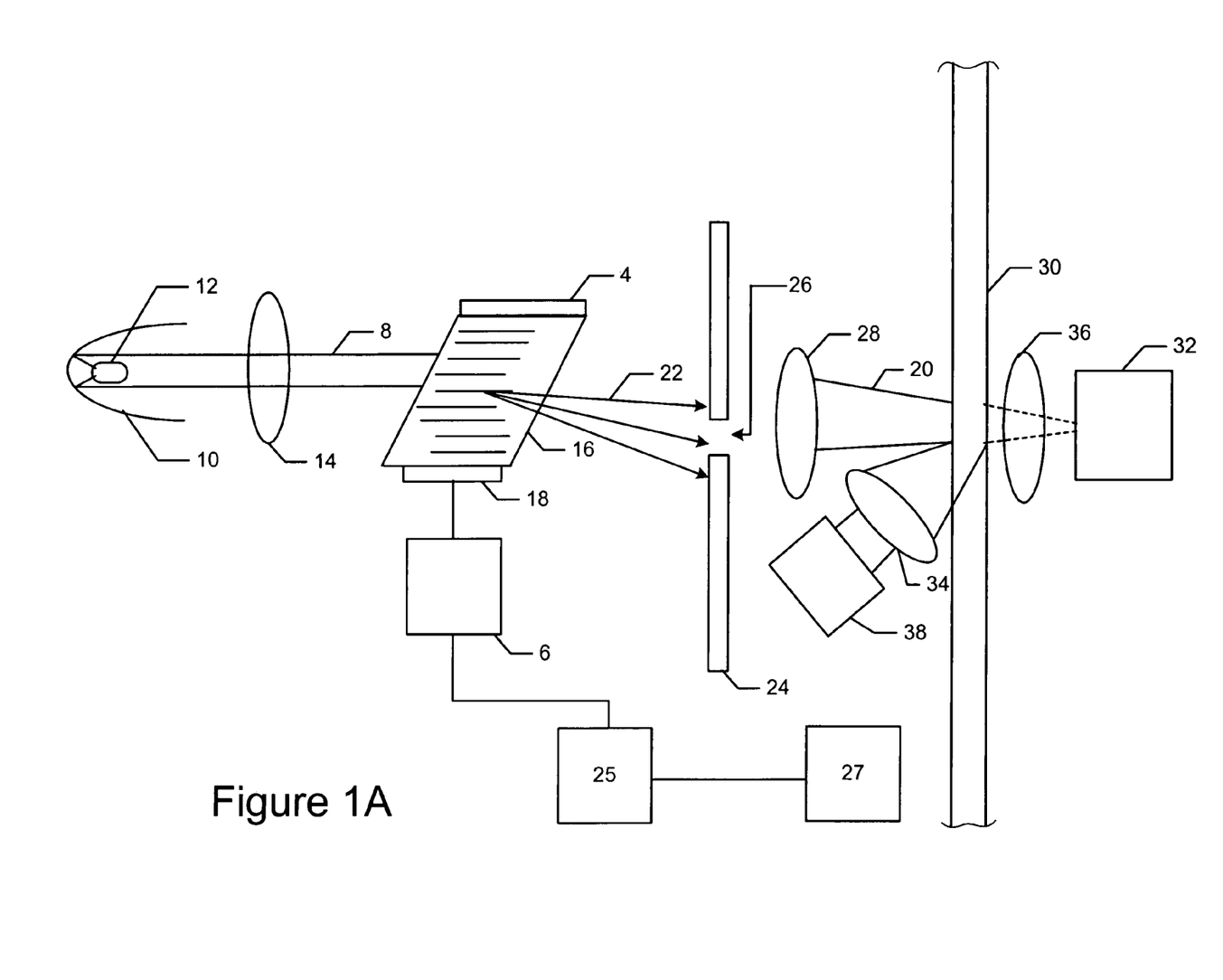
FIGS. 1A and 1B are schematic diagrams of two embodiments of the sensor apparatus of the present invention.

As shown in FIG. 1A, the sensor is employed to measure physical characteristics of a web of paper or plastic 30. Light from a broadband light source 12, e.g., white light source, is collimated using either lenses 14 and/or parabolic reflector 10. Suitable light sources include, for example, light emitting diodes (LED) and quartz tungsten halogen (QTH) lamps. The light can be modulated by direct amplitude modulation using conventional tuning forks or chopper wheels, if desired. If an LED source is used, modulation can be achieved directly via its drive current.

The collimated broadband light 8 is directed to an acousto-optic tunable filter (AOTF). For filtering light in the infrared radiation spectrum, e.g., wavelengths in the 1 to >4 µm range, the AOTF preferably comprises an acousto-optic crystal 16 such as tellurium dioxide ($TeO_2$) or lithium niobate ($LiNbO_3$) that has a piezoelectric transducer, such as a Lead Zirconate Titanate (PZT) 18, attached to one face of the crystal. A variable radio frequency (RF) generator 6 applies an RF signal to the PZT to cause refractive index modulation, e.g., a diffraction grating, to be is created within the acousto-optic crystal. Consequently, the broadband light 8 that passes through the modulated crystal is dispersed to form a spectrum of light 22 or a light beam with a swept wavelength. The degree of dispersion can be regulated by selecting the appropriate frequency of the applied RF signal. The RF signal can be applied transverse to the light 8. Acousto-optic tunable filters wherein the light signal and RF signal propagate collinearly can also be employed in the sensor. Preferably, the AOTF includes an acoustic absorber 4 that prevents unwanted back reflections of the RF signal. Suitable AOTFs are available from a number of manufacturers including, Brimrose Corp. (Baltimore Md.), Isomet (Springfield, Va.) and Gooch & Housego (U.K.).

A screen 24, that is made of material that is not transparent to the light 22, absorbs or reflects the light 22 except for a specific selected portion of light 22 which passes through an aperture or slit 26 in the screen 24. Light passing through the aperture 26 will have the desired bandwidth for analyzing one or more components of the sheet 30. As is apparent, changing the frequency of the RF signal that is applied to the crystal 16, shifts the wavelength of the radiation that passes through aperture 26. It is expected that infrared radiation within the wavelength range from 1 µm to >4 µm can be typically tuned from one wavelength to another within 10 s of microseconds. Alternatively, instead of changing the frequency of the RF signal, the screen 24 is moved to maneuver the aperture 26 to allow radiation of the desired bandwidth to pass through. A non-contact temperature sensor 27 is positioned adjacent the sheet to measure its temperature and temperature signals therefrom are communicated to or a controller 25 such as micro processor. When the temperature of the sheet changes, it may be necessary to adjust the center wavelength of the desired bandwidth to optimize detection. This case, the controller 25 changes the frequency of the RF signal from the RF generator 6.

In addition, as further described herein, the controller 25 can have a database that stores information regarding different components that can be detected, e.g., polymers, and their associated detection radiation bandwidth(s). Thus, the controller 25 can automatically change the RF signal from the generator 6 in order to detect different components.

Preferably, appropriate conditioning optics, e.g., focusing lens 28, are positioned to direct a beam of light 20 onto the web 30. Light emerges from the web 30 as scattered light or transmitted light. In one embodiment, the sensor employs a focusing lens 34 and detector 38 to measure the intensity of light that is scattered from the web 30. Alternatively, in conjunction with or instead of lens 34 and detector 38, the focusing lens 36 and detector 32 are used to measure the intensity of light that is transmitted through web 30.

Figure 1B:
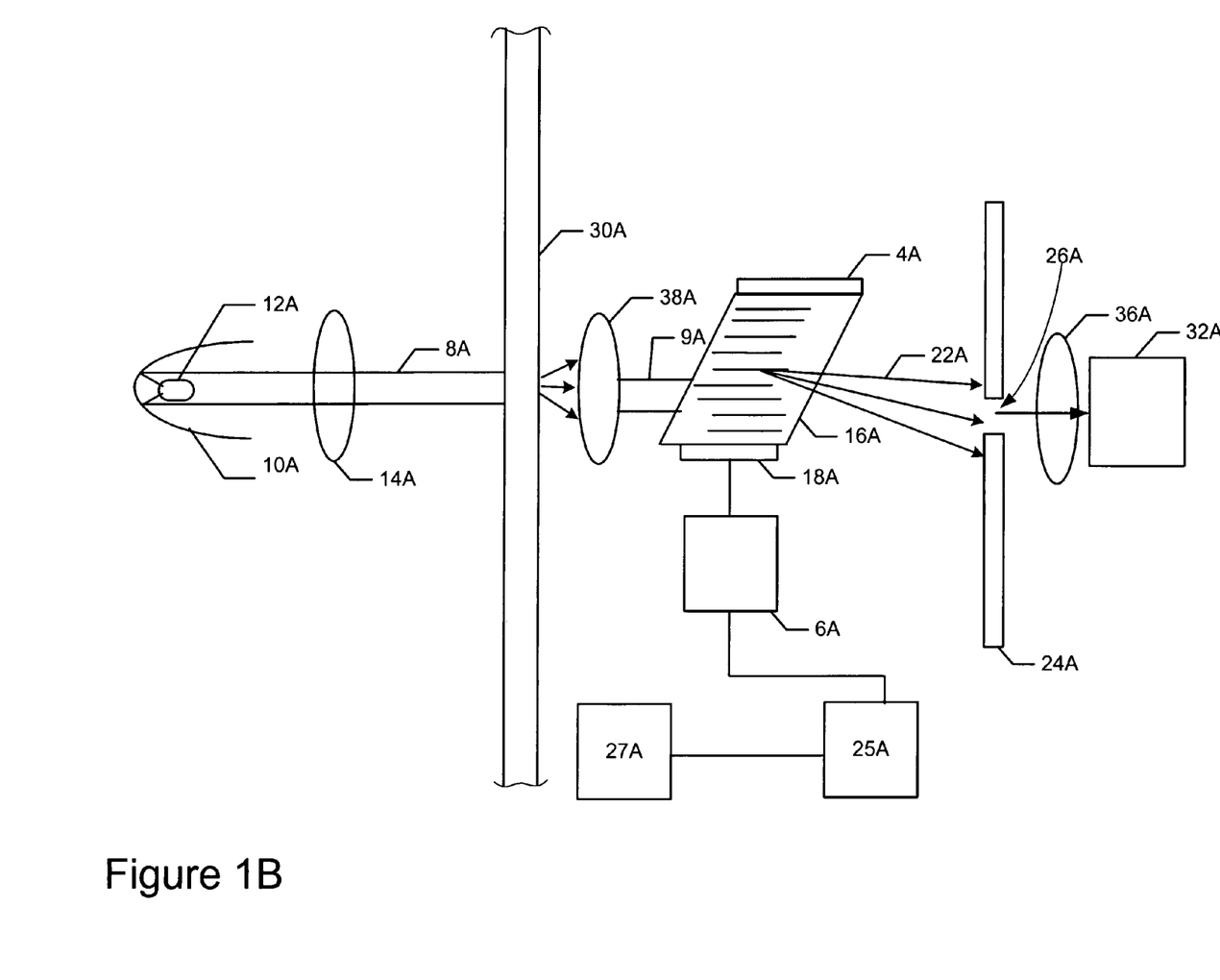

FIG. 1B, illustrates another embodiment of the sensor apparatus which is configured so that light emerging from the material being monitored is then directed to the AOTF. Light from a broadband light source 12A is collimated using either lenses 14A and/or parabolic reflector 10A. The collimated broadband light 8A is directed toward the sheet 30A. Light which passes through the sheet 30 is collimated by lens 38A to form a beam of light 9A into an AOTF that comprises an acousto-optic crystal 16A with a piezoelectric transducer (PZT) 18A attached to one face of the crystal. An RF generator 6A applies an RF signal to the PZT to cause refractive index modulation, e.g., a diffraction grating, to be is created within the acousto-optic crystal. Consequently, the broadband light 9A that passes through the modulated crystal is dispersed to form a spectrum of light 22A or a light beam with a swept wavelength. Preferably, the AOTF includes an acoustic absorber 4A that prevents unwanted back reflections of the RF signal.

A screen 24A absorbs or reflects the light 22A except for a specific selected portion of light 22A which passes through an aperture or slit 26A in the screen 24A. Light passing through the aperture 26A will have the desired bandwidth and center wavelength for analyzing one or more components of the sheet 30A. As is apparent, changing the frequency of the RF signal that is applied to the crystal 16A, shifts the wavelength of the radiation that passes through aperture 26A. Alternatively, instead of changing the frequency of the RF signal, the screen 24A is moved to maneuver the aperture 26A to allow radiation of the desired bandwidth to pass through. The apparatus further includes a non-contact temperature sensor 27A and controller 25A.

The apparatus as shown in FIG. 1B measures transmitted light. Alternatively, the apparatus can be configured to measured scattered light from the sheet 30A as shown in FIG. 1A.

The sensor apparatuses shown in FIGS. 1A and 1B can be readily configured to operate in the interferometric mode to measure the thickness of optically transparent films. Specifically, the AOFT is dynamically tuned over a range of wavelengths that can produce interference in the film. When the wavelength is continuously tuned over a wavelength range, a periodic intensity pattern as a function of wavelength is produced. An appropriate database can be accessed or software implemented in order to calculated the thickness of the film from the periodicity of the interference pattern that is produced.

Figure 2:
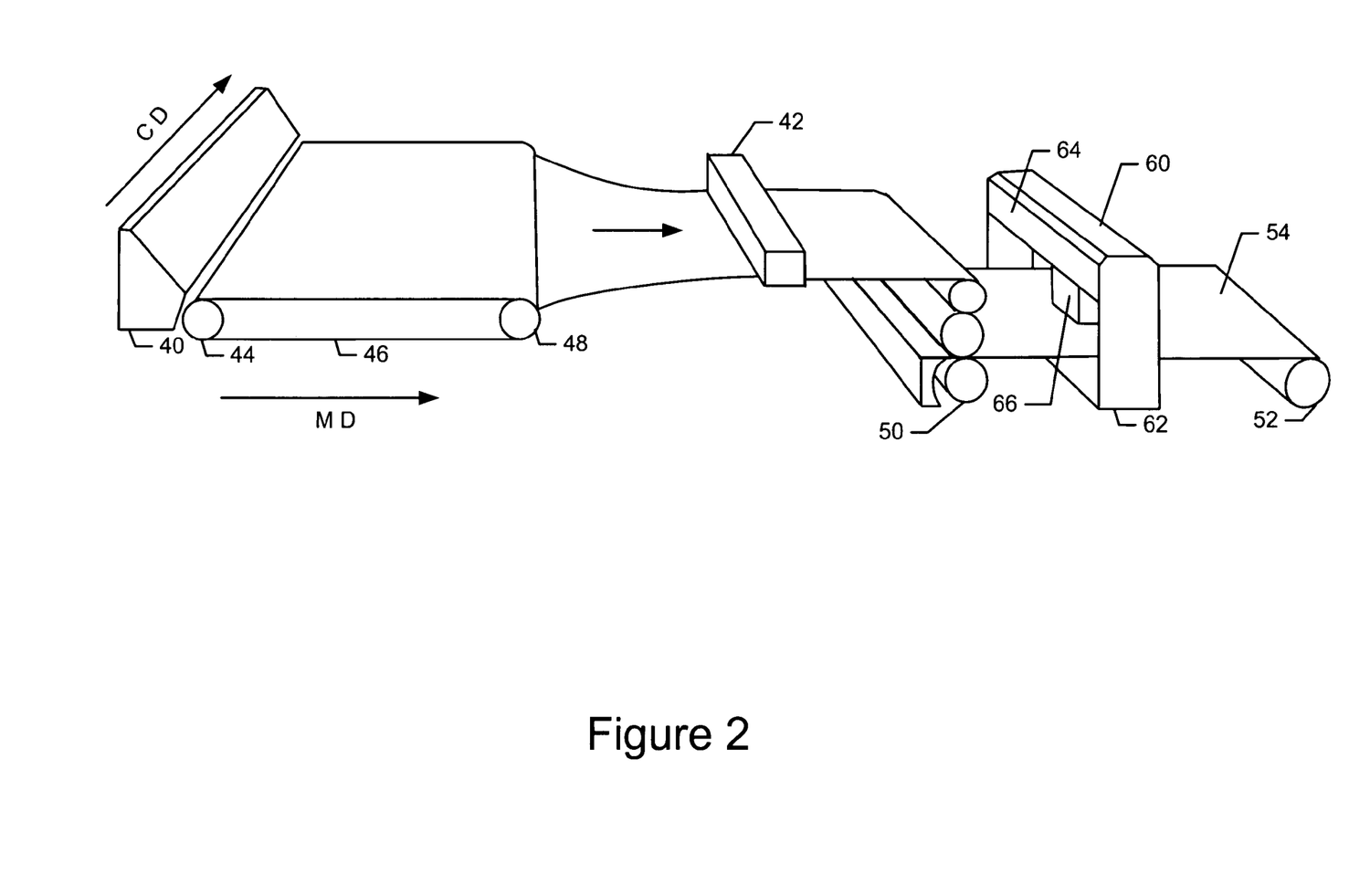
FIG. 2 illustrates a sheetmaking system including the sensor of the present invention.

In one embodiment, the inventive sensor can be used to measure physical characteristics of an aqueous mixture (referred to as wetstock) in a sheetmaking system. FIG. 2 shows a typical sheetmaking system for producing a continuous sheet of paper material 54 including a headbox 40, a steambox 42, a calendaring stack 50, a take-up reel 52 and scanner system 60 that includes the sensor. In the headbox 40, actuators are arranged to control discharge of wetstock onto supporting wire or web 46 along the cross direction (CD). The sheet of fibrous material that forms on top of the wire 46 is trained to travel in the machine direction (MD) between rollers 44 and 48 and passes through a calendaring stack 50. The calendaring stack 50 includes actuators that control the compressive pressure applied across the paper web. The system includes a press section (not shown) where water is mechanically removed from the sheet and where the web is consolidated. Thereafter, water is removed by evaporation in the dryer section (not shown). The finished sheet product 54 is collected on a reel 52. In practice, the portion of the paper making process near a headbox is referred to as the "wet end", while the portion of the process near a take-up reel is referred to as the "dry end". Papermaking machines are known in the art and are described, for example in U.S. Pat. No. 6,780,284 which is incorporated herein.

The scanner system 60 generally includes pairs of horizontally extending guide tracks 64 that span the width of the paper product 54. The guide tracks are supported at their opposite ends by upstanding stanchions 62 and are spaced apart vertically by a distance sufficient to allow clearance for paper product 54 to travel between the tracks. The sensor is secured to a carriage 66 that moves back-and-forth over to paper product 54 as measurements are made. On-line scanning sensor systems for papermaking manufacture are disclosed in U.S. Pat. No. 4,879,471 to Dahlquist, U.S. Pat. No. 5,094,535 to Dahlquist et al., and U.S. Pat. No. 5,166,748 to Dahlquist, all of which are incorporated herein fully by reference.

Infrared (IR) spectroscopy is a technique for moisture content measurement. One approach is to predetermine absorption and reference IR wavelengths of interest and to employ the inventive sensor to provide a constant, reliable, stream of energy within the wavelengths required to yield suitable water weight measurement. Specifically, water absorbs radiation across the infrared spectrum as a function of wavelength. The higher the moisture content in a sheet, the less radiation at or near the water absorption peak that will pass through or be reflected from the sheet.

The sensor can initially measure the intensity of radiation that emerges from a sheet of paper using the absorption IR band wavelength. Thereafter, by changing the RF signal that is applied to the AOTF, IR radiation at the reference band wavelength is directed to the sheet of paper and its intensity measured. In effect, the first measurement is primarily sensitive to the amount of water in the sheet and more infrared radiation is measured when the sheet is dry and less infrared radiation when the sheet is moist. Conversely, for the second measurement, the radiation is in an IR band wavelength where there is less moisture absorption. The light loss in this band is due to non-water dependent losses from the sheet. These loses are primarily due to scattering from the sheet as well as non-water dependent attenuation factors of the sheet. Thus, when the basis weight, i.e., weight per unit area, of the sheet fiber increases, the second measurement detects less infrared radiation. The second measurement corrects for non-water dependent losses from the sheet.

The inventive sensor can be readily optimized to adjust to the changing dynamics in the environment in which it operates. For example, it is known that the absorption or sensing center wavelength for moisture in paper is typically 1.93 μm and the reference wavelength is typically 1.84 μm at typical ambient conditions, but the absorption wavelength is temperature dependent. In other words, the optimum absorption wavelength changes with temperature. One technique of maintaining accurate and precise measurements despite temperature fluctuations in the paper is to shift the center wavelength while keeping the optimum bandwidth. Thus, as the temperature of the paper changes, the frequency of the RF signal is adjusted to appropriately shift the wavelength of the radiation such that the absorption IR remains centered on the most sensitive region of the spectral absorption. This effectively preserves the sensor's moisture sensitivity while compensating for temperature changes. With prior art spectroscopic sensors that use discrete filters, it was necessary to increase filter bandwidth in order to temperature desensitize the sensor. Unfortunately, this also compromises the sensor's sensitivity to moisture.

Besides measuring moisture content, other physical characteristics of the sheet material can also be monitored. These components include, for example, fibers, such as cellulose, latex, minerals, e.g., $CaCO_3$ and clay, and the like. In each case, selecting the proper radiation region, e.g., IR bandwidth, is required. IR absorption by different components in paper and paper coated products are further described in U.S. Pat. No. 5,013,403 to Chase, U.S. Pat. No. 5,235,192 to Chase et al., and U.S. Pat. No. 5,795,394 to Belotserkovsky et al., which are incorporated herein fully by reference.

One or more sensors of the present invention can be employed to optimize papermaking machines. Process control techniques for papermaking machines are further described, for instance, in U.S. Pat. No. 6,149,770 to Hu et al., U.S. Pat. No. 6,092,003 to Hagart-Alexander et. al, U.S. Pat. No. 6,080,278 to Heaven et al., U.S. Pat. No. 6,059,931 to Hu et al., U.S. Pat. No. 6,853,543 to Hu et al., and U.S. Pat. No. 5,892,679 to He, which are all incorporated herein fully by reference.

As is apparent, a number of parameters of the wet end and dry end of the papermaking machine as illustrated in FIG. 2 can be regulated. For example, with the scanner system 60 a continuous moisture profile of the paper can be generated and compared to an "ideal" profile for making a particular grade of paper. Depending on the degree of deviation from ideal, wet end and/or dry end parameters can be adjusted accordingly. See, for example, U.S. Pat. No. 6,092,003 to Hagart-Alexander which is incorporated herein. Dry end and wet end parameters such as moisture profiles can be controlled using actuator such as steam boxes or re-wet showers.

Figure 3:
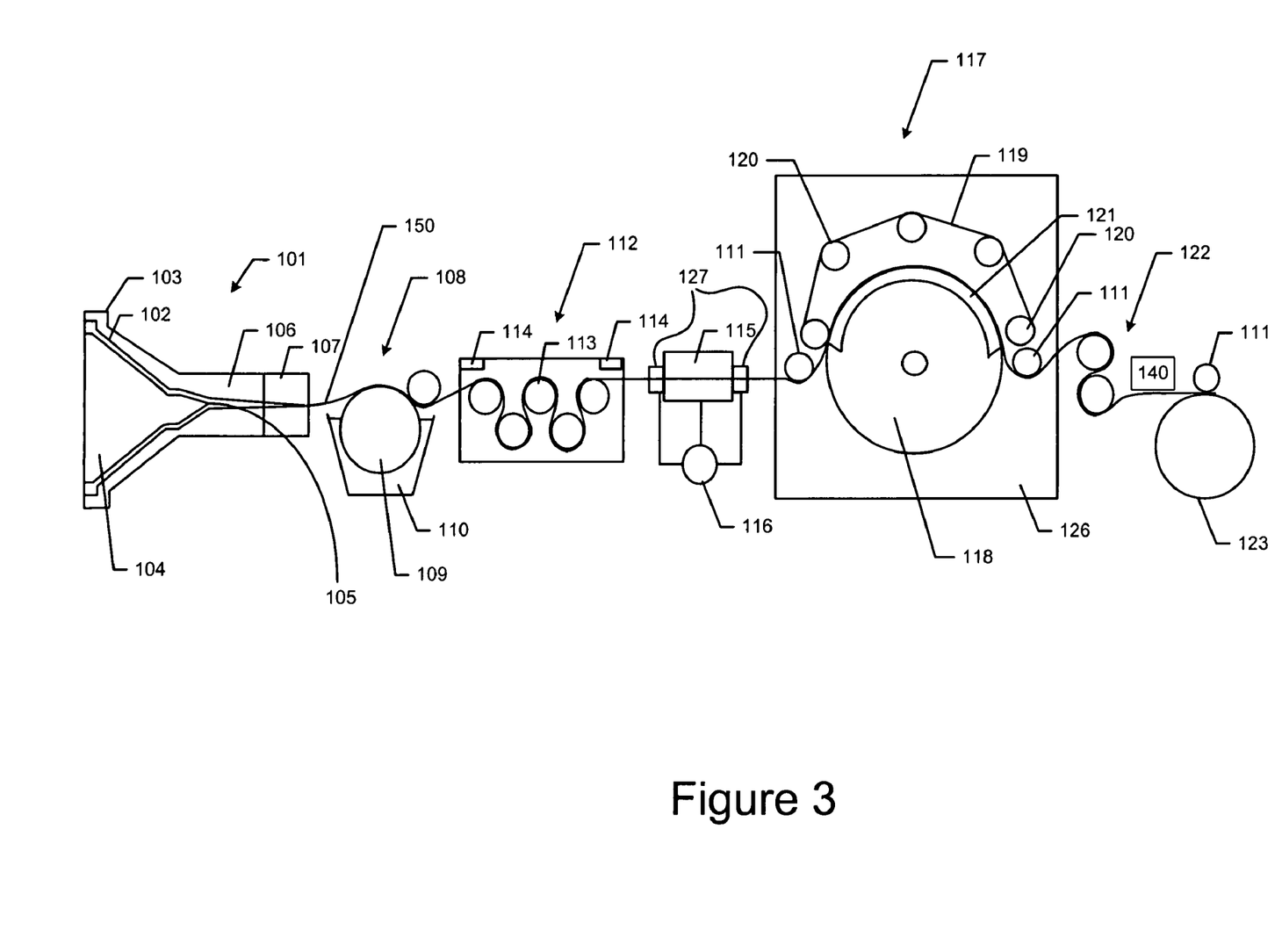
FIG. 3 illustrates the side view of a plastic film fabricating apparatus.

In another embodiment, the inventive sensor 140 can be used to measure the concentration of polymer in films that are formed in a continuous plastic production process. FIG. 3 illustrates an apparatus, for making plastic films, that includes a conical extruder 101 that comprises a cone-shaped rotor 102, an outer stator 103, and an inner stator 104. When the rotor 102 rotates, it extrudes material which is between the rotor 102 and the stators 103 and 104 from the extruder 101. The end portion of the inner stator 104 is wide and tapers in the vertical direction so that together with the nozzle 106 it forms a relatively flat and wide gap through which plastic 105 is extruded. After the nozzle 106 there is a calibration piece 107 whose nuts are used for adjusting the height of the gap, which allows to define the thickness of the plastic film 150 to be obtained from the extruder 101.

After exiting the extruder 101, the plastic film 150 is cooled by a cooling device 108 that may comprise a cooling roll 109, which is arranged in a cooling tank 110 containing water. The plastic film 150 is arranged to be pressed against the cooling roll 109. The apparatus has auxiliary rolls 111 for guiding the plastic film 105 at several points.

After being cooled, the plastic film 150 is guided to a machine direction orientation device 112 that includes orientation rolls 113 whose velocities are adjusted so that they can be used for stretching the plastic film 150 and heating means 114, such as radiation heaters, for heating the plastic film 150. Subsequently, the plastic film 150 moves into a discharge chamber 115 which contains pressurized air that is fed by a pump 116. A sealing chamber 127 is provided at the forward end and at the tail end of the discharge chamber 115. When the pressure in the discharge chamber 115 is increased with the pump 116, the temperature also rises as gas is compressed. This heat can be utilized to heat the plastic film 150. The discharge chamber 115 may also be provided with heating resistors which are arranged to heat the plastic film 150. Thus the discharge chamber 115 can be used both for feeding gas into the plastic film and for heating the plastic film 150 for orientation in the cross-direction.

When materials are added to the plastic cavitation bubbles can be formed. When the plastic film 150 is subjected to the pressure of pressurized gas after orientation, the gas diffuses in the cavitation bubbles and causes overpressure in the bubbles. In the discharge chamber 115 the pressurized gas can act on both sides of the plastic film 150, and thus gas bubbles are formed evenly in the plastic film 150.

Next, the plastic film 150 entered into a cross-direction orientation device 117 where the plastic film 150 is stretched in the cross-direction which is transverse to the direction of the orientation performed in the machine direction device 112. The cross-direction orientation device 117 comprises two orientation wheels 118, and an orientation band 119 is arranged against both of the wheels. The orientation band 119 is an endless band which is guided by means of band guide rolls 120. The orientation band 119 presses the edges of the plastic film 150 firmly and evenly between the orientation wheel 118 and the orientation band 119 substantially along the whole travel the cross-direction orientation device 117, in which case the film is not subjected to varying pressure stress or tensile strain, and thus the plastic film stretches sideways without tearing. The cross-direction orientation device 117 can be positioned within a casing 126. Finally, the plastic film 150 is led to a relaxation unit 122 where the plastic film 150 is relaxed and is wound on a reel 123.

As shown in FIG. 3, a sensor 140 of the present invention is positioned to monitor the plastic film before being wound on the reel 123. It is understood that the sensor 140 can be positioned anywhere along the production line as desired. The inventive sensor can be employed with any suitable apparatus for continuous production of plastic films known in the art. Representative machines are further described, for instance, in U.S. Pat. No. 6,793,854 to Kirjavainen, U.S. Pat. No. 6,565,343 to Krycki, U.S. Pat. No. 5,230,923 to Hirokawa et al., U.S. Pat. No. 4,797,246 to Reinke et al., and U.S. Pat. No. 4,311,658 which are incorporated herein by reference.

A preferred application of the sensor 140 is to monitor the thickness of the film by measuring the concentration(s) (weights per unit area, typically measured in grams per square meter, gsm) of the particular polymer(s) that form the film. In the case where the film consists of a single layer of one polymer, the sensor 140 is set to direct radiation, e.g., IR radiation, of the appropriate bandwidth to measure the polymer. In the case where the plastic is a single layer that comprises a blend of two or more different polymers or where the plastic is a multilayer film, then the AOTF in the sensor can be programmed to continuously change bandwidth in order to measure the different polymers that are present. Alternatively, the AOFT (via the RF generator) can be programmed to sequentially step through the particular wavelength bands of interest for the particular components of interest within the plastic film. Multilayer films typically comprise a plurality of layers that are laminated together. Preferably, in the multilayer structure, adjacent layers are formed of different polymer materials. By employing different polymers with different physical properties, the multilayer film may have a combination of physical attributes not present in a single layer film. For example, the multilayer film may be moisture resistant, abrasion resistant, and yet remain pliable. The sensor of the present invention, among other things, is effective in controlling the production of multilayer films to assure that each layer in the film has the proper thickness or weight (gsm) so that the multilayer film has the right combination of properties. A number of AOFT sensors as described above can be employed in order to process data in parallel.

Each polymer has absorption peaks at specific wavelengths. By creating a database or otherwise programming the controller in the sensor, the bandwidth of the radiation from the sensor be sequentially switch through each of the wavelengths in order to measure the polymers of interest. If the density of a particular polymer component in the multilayer film is known the the thickness of the film component can be determined. The thickness can be calculated with a computer. Commonly the film thickness is not calculated and the weight (gsm) of the component is all that is required by the user for quality control.

The foregoing has described the principles, preferred embodiment and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of present invention as defined by the following claims.

What is claimed is:

1. A sensor, for measuring at least one component in a composition, that comprises:
    a broadband light source that generates light;
    an acousto-optic tunable filter (AOTF);
    optics that direct a beam of light at the AOTF, wherein the AOTF is tuned to pass detection light having a desired wavelength range to detect a concentration of the at least one component in the composition;
    a screen that directs the detection light of known wavelength to the composition;
    a detector that receives light that emerges from the composition; and
    a control signal generator that provides the AOTF with at least one desired wavelength range that is characteristic of the least one component in the composition;
    wherein the composition comprises paper, and wherein the sensor detects at least one of: a level of cellulose in the paper, a level of calcium carbonate in the paper or paper coating, a level of clay in the paper or paper coating, and a level of latex in the paper or paper coating.

2. The sensor of claim 1 further comprising:
    a persistent store coupled to the control signal generator, wherein the persistent store provides the control signal generator with the at least one desired wavelength range.

3. The sensor of claim 1 further comprising:
    a temperature sensor that measures a temperature of the composition and generates temperature signals indicative thereof; and
    a controller, responsive to the temperature signals, that adjusts the at least one desired wavelength range in order to optimize a sensitivity to the at least one component being measured.

4. The sensor of claim 1 wherein the detector is positioned to detect an intensity of light that is reflected from the composition.

5. The sensor of claim 1 wherein the detector is positioned to detect an intensity of light that is transmitted through the composition.

6. The sensor of claim 1 wherein the AOTF generates a light beam having a swept wavelength, and the screen comprises an aperture through which the detection light passes to the composition.

7. The sensor of claim 6 further comprising alignment means for optically aligning the light beam having a swept wavelength to the aperture.

8. The sensor of claim 6 further comprising alignment means for optically aligning the light beam having a sequential step through a finite number of discrete wavelength ranges to the aperture.

9. The sensor of claim 8 wherein the aperture at least partially blocks visible light but is transparent to infrared radiation.

10. The sensor of claim 8 wherein the aperture at least partially blocks infrared light outside a particular infrared band of interest.

11. The sensor of claim 1 wherein the AOTF is controlled with a variable frequency radio frequency (RF) generator.

12. sensor of claim 1 wherein the sensor further detects a level of water in the paper.

13. The sensor of claim 1 wherein the sensor further measures at least one component in a second composition, wherein the second composition comprises plastic.

14. The sensor of claim 13 wherein the sensor detects a concentration of at least one polymer in the plastic.

15. A sensor, for measuring at least one component in a composition, that comprises:
    a broadband light source that generates light that is directed to the composition;
    an acousto-optic tunable filter (AOTF) positioned to receive light that emerges from the composition, wherein the AOTF is tuned to pass detected light having a desired wavelength range to detect a concentration of the at least one component in the composition;
    a detector that receives the detected light; and
    a control signal generator that provides the AOTF with at least one desired wavelength range that is characteristic of the least one component in the composition;
    wherein the composition comprises paper, and wherein the sensor detects at least one of: a level of cellulose in the paper, a level of calcium carbonate in the paper or paper coating, a level of clay in the paper or paper coating, and a level of latex in the paper or paper coating.

16. The sensor of claim 15 further comprising:
    a persistent store coupled to the control signal generator, wherein the persistent store provides the control signal generator with the at least one desired wavelength range.

17. The sensor of claim 15 further comprising:
    a temperature sensor that measures a temperature of the composition and generates temperature signals indicative thereof; and
    a controller, responsive to the temperature signals, that adjusts the at least one desired wavelength range in order to optimize an intensity of light that is received by the detector.

18. The sensor of claim 15 wherein the AOTF is positioned to receive light that is reflected from the composition.

19. The sensor of claim 15 wherein the AOTF is positioned to detect light that is transmitted through the composition.

20. The sensor of claim 15 wherein the AOTF generates a light beam having a swept wavelength, and the sensor further comprises an aperture through which light having the desired wavelength range passes to the detector.

21. The sensor of claim 20 further comprising alignment means for optically aligning the light beam having a swept wavelength to the aperture.

22. The sensor of claim 21 wherein the aperture at least partially blocks visible light but is transparent to infrared radiation.

23. The sensor of claim 21 wherein the aperture at least partially blocks infrared light outside a particular infrared band of interest.

24. The sensor of claim 15 wherein the AOTF is controlled with a variable frequency radio frequency (RF) generator.

25. The sensor of claim 15 wherein the sensor further detects a level of water in the paper.

26. The sensor of claim 15 wherein the sensor detects the level of cellulose in the paper.

27. The sensor of claim 15 wherein the sensor detects the level of calcium carbonate in the paper or paper coating.

28. The sensor of claim 15 wherein the sensor detects the level of clay in the paper or paper coating.

29. The sensor of claim 15 wherein the sensor detects the level of latex in the paper or paper coating.

30. The sensor of claim 15 wherein the sensor further measures at least one component in a second composition, wherein the second composition comprises plastic.

31. The sensor of claim 30 wherein the sensor detects a concentration of at least one polymer in the plastic.

32. A method for measuring an amount of at least one component of a composition tat comprises the steps of:
  directing broadband light to an acousto-optic tunable filter (AOTF);
  tuning the AOTF to pass first detection light having a desired wavelength to detect a concentration of a first component in the composition;
  directing the first detection light to the composition;
  detecting an intensity of the first detection light that emerges from the composition;
  tuning the AOTF to change the wavelength of the detection light to generate second detection light to measure a second component in the composition;
  directing the second detection light to the composition;
  detecting an intensity of the second detection light that emerges from to composition; and
  determining an amount of at least one of the components of the composition using the intensities of the first and second detection light;
  wherein the composition comprises paper, and wherein determining the amount of at least one of the components comprises detecting at least one of: a level of cellulose in the paper, a level of calcium carbonate in the paper or paper coating, a level of clay in the paper or paper coating, and a level of latex in the paper or paper coating.

33. A method for measuring an amount of at least one component of a composition that comprises the steps of:
  directing broadband light to the composition;
  directing light that emerges from the composition into an acousto-optic tunable filter (AOTF);
  tuning the AOTF to pass first detection light having a desired wavelength to detect a presence of a first component in the composition;
  detecting an intensity of the first detection light that emerges from the composition;
  tuning the AOTF to change the wavelength of the detection light to generate second detection light to measure a second component in the composition;
  detecting an intensity of the second detection light that emerges from the composition; and
  determining an amount of at least one of the components of the composition using the die intensities of the first and second detection light;
  wherein the composition comprises paper, and wherein determining the amount of at least one of the components comprises detecting at least one of: a level of cellulose in the paper, a level of calcium carbonate in the paper or paper coating, a level of clay in the paper or paper coating, and a level of latex in the paper or paper coating.

34. The sensor of claim 1, wherein the optics comprise at least one of: one or more lenses and a parabolic reflector.

35. The method of claim 32, further comprising:
  repeating the directing and detecting steps associated with the second detection light using one or more different wavelengths in order to measure one or more components other than the first and second components; and
  measuring a temperature of the composition and changing the wavelength of at least one of the first and second detection light to optimize an intensity of at least one of the first and second detection light that is measured.

* * * * *

UNITED STATES PATENT AND TRADEMARK OFFICE
CERTIFICATE OF CORRECTION

PATENT NO. : 7,321,425 B2 Page 1 of 1
APPLICATION NO. : 11/018167
DATED : January 22, 2008
INVENTOR(S) : Frank M. Harran It is certified that error appears in the above-identified patent and that said Letters Patent is hereby corrected as shown below:

In Column 14, line 21, delete "die".

Signed and Sealed this

Thirteenth Day of May, 2008

JON W. DUDAS
*Director of the United States Patent and Trademark Office*